(12) United States Patent
Ecker (10) Patent No.: US 11,452,392 B1
(45) Date of Patent: Sep. 27, 2022

(54) SYSTEM, APPARATUS, AND METHOD FOR SUPPORTING A BODY

(71) Applicant: Lloyd Ecker, Pomona, NY (US)

(72) Inventor: Lloyd Ecker, Pomona, NY (US)

( * ) Notice: Subject to any disclaimer, the term of this patent is extended or adjusted under 35 U.S.C. 154(b) by 0 days.

(21) Appl. No.: 17/726,929

(22) Filed: Apr. 22, 2022

(51) Int. Cl.
*A47G 9/10* (2006.01)
*A61F 5/56* (2006.01)
*A47C 7/36* (2006.01)
*A47C 20/02* (2006.01)
*A61G 7/065* (2006.01)
*A61G 13/12* (2006.01)

(52) U.S. Cl.
CPC .............. *A47G 9/1072* (2013.01); *A47C 7/36* (2013.01); *A47C 20/027* (2013.01); *A61F 5/56* (2013.01); *A61G 7/065* (2013.01); *A61G 13/12* (2013.01); *A47G 9/10* (2013.01); *A47G 2009/1018* (2013.01)

(58) Field of Classification Search
CPC .......... A47G 9/1072; A47G 9/10; A47C 7/36; A47C 7/38; A47C 20/027; A47C 20/02; A47C 20/00; A61G 7/065; A61G 7/07; A61G 13/12; A61G 13/121; A61G 13/1225; A61F 5/56
USPC .... 5/636, 637, 640, 632–634, 630, 657, 652
See application file for complete search history.

(56) References Cited

U.S. PATENT DOCUMENTS

| | | | |
|---|---|---|---|
| 2,877,472 A * | 3/1959 | Wagner | A47G 9/10 5/636 |
| 4,074,376 A | 2/1978 | Bond | |
| 4,118,813 A | 10/1978 | Armstrong | |
| 4,210,317 A * | 7/1980 | Spann | A61G 13/12 482/142 |
| 4,275,473 A * | 6/1981 | Poirier | A47C 27/146 5/699 |
| 4,441,221 A | 4/1984 | Enste | |
| 4,736,477 A * | 4/1988 | Moore | A47C 20/021 128/892 |
| 4,850,067 A | 7/1989 | Latorre | |
| 5,127,120 A | 7/1992 | Mason | |
| D333,752 S | 3/1993 | Mason | |
| 5,432,967 A | 7/1995 | Raftery | |
| 5,669,089 A * | 9/1997 | Dees | B25H 5/00 5/722 |
| D398,181 S | 9/1998 | Lange | |
| D400,386 S | 11/1998 | Keilhauer | |
| 5,950,260 A * | 9/1999 | Dees | B25H 5/00 5/419 |
| 6,052,847 A * | 4/2000 | Allyn | A47C 20/027 5/632 |
| 6,226,817 B1 | 5/2001 | Rubio | |
| 6,360,387 B1 | 3/2002 | Everhart | |
| 6,618,883 B2 * | 9/2003 | Angland | A47C 17/04 5/659 |

(Continued)

*Primary Examiner* — Robert G Santos
(74) *Attorney, Agent, or Firm* — Stephen L. Keefe LLC (57) ABSTRACT

An apparatus for supporting a human body is disclosed. The apparatus has a body assembly configured to support a back of the human body, a head assembly attached to the body assembly via an attachment portion, the head assembly including one or more members forming a recess configured to receive a head of the human body, and a slit disposed between the body assembly and the head assembly, the slit configured to open from a closed position to an open position to provide rotation of the head assembly relative to the body assembly.

20 Claims, 6 Drawing Sheets

(56) References Cited

U.S. PATENT DOCUMENTS

| | | | | |
|---|---|---|---|---|
| 6,640,368 B2 * | 11/2003 | Roston | ............... | A47C 20/021 5/655.9 |
| 6,957,497 B2 | 10/2005 | Greenawalt | | |
| D521,301 S | 5/2006 | Dickson | | |
| D543,064 S | 5/2007 | Hale | | |
| 7,581,267 B2 | 9/2009 | Rubio | | |
| D642,412 S | 8/2011 | Cuba | | |
| 8,127,385 B1 | 3/2012 | Goutevenier | | |
| D712,677 S | 9/2014 | Clute | | |
| D753,312 S | 4/2016 | Long | | |
| 9,700,147 B2 | 7/2017 | Kim Thi Pham | | |
| D800,852 S | 10/2017 | Flook | | |
| D805,325 S | 12/2017 | Chan | | |
| D821,780 S | 7/2018 | Strandberg | | |
| 10,244,877 B2 * | 4/2019 | Bradshaw | ............ | A47G 9/1063 |
| D864,612 S | 10/2019 | Castellano | | |
| D882,296 S | 4/2020 | Huang | | |
| D907,941 S | 1/2021 | Chanfrau, IV | | |
| D929,153 S | 8/2021 | Carver | | |
| 11,160,398 B2 | 11/2021 | Chan | | |
| 2003/0046767 A1 * | 3/2003 | Roston | ............... | A47C 20/021 5/648 |
| 2003/0140423 A1 * | 7/2003 | Angland | ............... | A47C 17/04 5/659 |
| 2008/0163427 A1 * | 7/2008 | Howe | ............... | A47C 20/027 5/634 |
| 2014/0096777 A1 | 4/2014 | Derner | | |
| 2014/0245540 A1 | 9/2014 | Oh | | |
| 2016/0081500 A1 * | 3/2016 | Bradshaw | ............... | A47G 9/10 5/640 |
| 2021/0030583 A1 | 2/2021 | Chanfrau, IV | | |

* cited by examiner

Fig. 2A
UNEXTENDED MODE

Fig. 8
UNEXTENDED MODE

Fig. 9
EXTENDED MODE

Fig. 9A
EXTENDED MODE

Fig. 10
UNEXTENDED MODE

Fig. 11
EXTENDED MODE

Fig. 12
UNEXTENDED MODE

SYSTEM, APPARATUS, AND METHOD FOR SUPPORTING A BODY

TECHNICAL FIELD

The present disclosure generally relates to a system, apparatus, and method for support, and more particularly to a system, apparatus, and method for supporting a body.

BACKGROUND

Sleeping conditions and disorders such as snoring and sleep apnea pose health risks to many people. These conditions and disorders deprive many people of adequate sleep, which often leads to more serious health problems. For example, these conditions and disorders may increase cardiovascular risk.

Conventional systems exist for attempting to address sleeping conditions and disorders such as snoring and sleep apnea. For example, some of these conventional systems attempt to position people at risk for such conditions and disorders to be at beneficial body positions during sleep.

U.S. patent application number 2021/0030583 to Chanfrau, I V (the '583 publication) attempts to address some of the above shortcomings in the prior art. The '583 publication discloses a stepped pillow for positioning the user's head during sleep. However, the stepped pillow of the '583 publication does not maintain a user's head stationary, which may result in negative effects for the user's sleep and health based on movement of the user's head. Also, the stepped pillow of the '583 publication does not allow for a user to adjustably attain a stationary position of the user's head, which decreases the effectiveness of the stepped pillow for treating sleeping conditions and disorders such as snoring and sleep apnea.

The exemplary disclosed system, apparatus, and method of the present disclosure are directed to overcoming one or more of the shortcomings set forth above and/or other deficiencies in existing technology.

SUMMARY OF THE DISCLOSURE

In one exemplary aspect, the present disclosure is directed to an apparatus for supporting a human body. The apparatus includes a body assembly configured to support a back of the human body, a head assembly attached to the body assembly via an attachment portion, the head assembly including one or more members forming a recess configured to receive a head of the human body, and a slit disposed between the body assembly and the head assembly, the slit configured to open from a closed position to an open position to provide rotation of the head assembly relative to the body assembly.

In another aspect, the present disclosure is directed to a method for supporting a human body. The method includes providing an apparatus including a body assembly and a head assembly attached to the body assembly via an attachment portion, the apparatus including a slit disposed between the body assembly and the head assembly, supporting a back of the human body with the body assembly, supporting a head of the human body with the head assembly, rotating the head assembly relative to the body assembly based on opening and closing the slit between a closed position and an open position, and maintaining the head in the head assembly based on receiving the head in a recess formed in the head assembly.

DETAILED DESCRIPTION AND INDUSTRIAL APPLICABILITY

The exemplary disclosed system, apparatus, and method may include an apparatus that may be changed between a plurality of positions to facilitate supporting a user's body. FIGS. 1-7 illustrate an apparatus 105 of a system 100.

Apparatus 105 may include a head assembly 110 and a body assembly 115. Head assembly 110 may support a head of a user supported by apparatus 105. Body assembly 115 may support a body of a user supported by apparatus 105. Head assembly 110 may be movable relative to body assembly 115 for example as described below.

Figure 1:
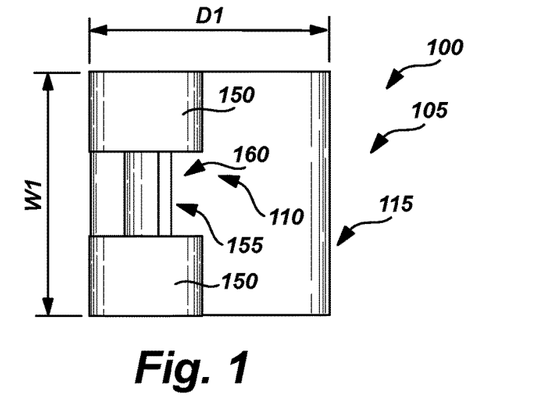
FIG. 1 is a top view of an exemplary embodiment of the present invention.
Figure 1A:
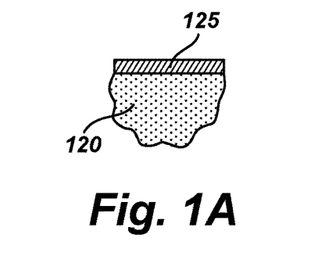
FIG. 1A is a sectional view of an exemplary embodiment of the present invention.

Head assembly 110 and body assembly 115 may be formed from any suitable material for supporting a user such as a body of a human user. For example as illustrated in FIG. 1A, head assembly 110 and body assembly 115 may include an inner portion 120 that may be covered by a cover portion 125. Cover portion 125 may be a relatively thin layer compared to inner portion 120 that may comfortably support a user being supported by head assembly 110 and body assembly 115.

Inner portion 120 of head assembly 110 and body assembly 115 may include elastic or flexible material. Inner portion 120 may include open-cell material, gel material, and/or multi-layer material. Inner portion 120 may include elastomeric material, rubber, foam material (e.g., open cell foam sheet material), and/or any other suitable elastic material. Inner portion 120 may include elastic material (e.g., rubber, foam, elastomeric material, polyester fiberfill, microbeads, and/or any other suitable elastic material) that may deform to comfortably fit a user's body. Inner portion 120 may include any suitable polymer material. In at least some exemplary embodiments, inner portion 120 may include polyurethane material. Inner portion 120 may include viscoelastic polyurethane foam and/or or low-resistance polyurethane foam. In at least some exemplary embodiments, inner portion 120 may be viscoelastic memory foam.

Inner portion 120 may be formed (e.g., configured) to provide any desired shape of head assembly 110 and body assembly 115 for supporting a user such as, for example, as illustrated in FIGS. 1-7. Inner portion 120 may be covered with cover portion 125 that may be a relatively thin layer formed from any suitable material that may feel comfortable to a user (e.g., to a user's skin). For example, cover portion 125 may be formed from textile or fabric (e.g., cotton, polyester, silk, and/or any other suitable textile or fabric material), felt, natural fiber material, synthetic fiber material, cotton, and/or any other suitable material that may feel comfortable to a user. For example, cover portion 125 may provide a covering to head assembly 110 and body assembly 115 that may be formed (e.g., configured and shaped) using inner portion 120.

Body assembly 115 may be shaped, dimensioned, and/or configured in any suitable shape for comfortably supporting a user's body for example to facilitate rest, comfort, and/or sleep of the user. For example, body assembly 115 may be formed with a depth D1 and a width W1. Depth D1 may be any suitable dimension for comfortably supporting a user's body such as, for example, between about 15 inches and about 40 inches, between about 16 inches and about 25 inches, or between about 16 inches and about 20 inches. Width W1 may be any suitable dimension for comfortably supporting a user's body such as, for example, between about 12 inches and about 40 inches, between about 14 inches and about 25 inches, or between about 15 inches and about 20 inches. A rear portion 130 of body assembly 115 may include a cutout of any suitable dimensions such as, for example, a cutout dimension C1 and a cutout dimension C2. Cutout dimensions C1 and C2 may be any suitable dimensions such as, for example, between about 2 inches and about 8 inches, or between about 2 inches and about 6 inches (e.g., about 4 inches).

Figure 10:
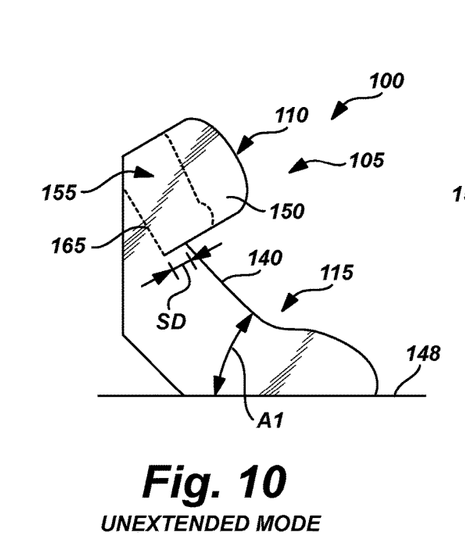
FIG. 10 is a side view of an exemplary embodiment of the present invention.
Figure 11:
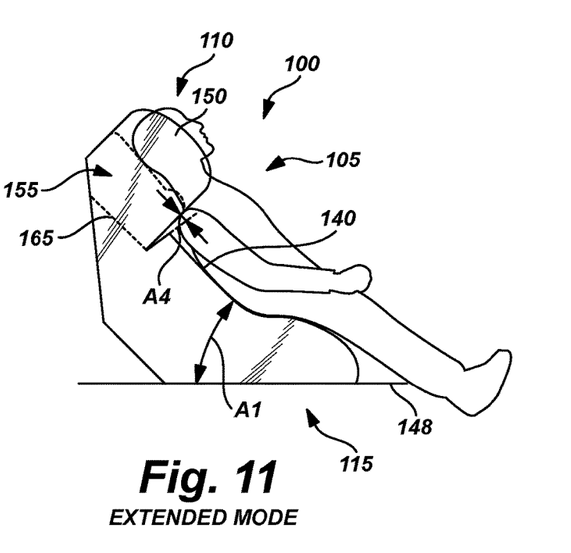
FIG. 11 is a side view of an exemplary embodiment of the present invention.
Figure 12:
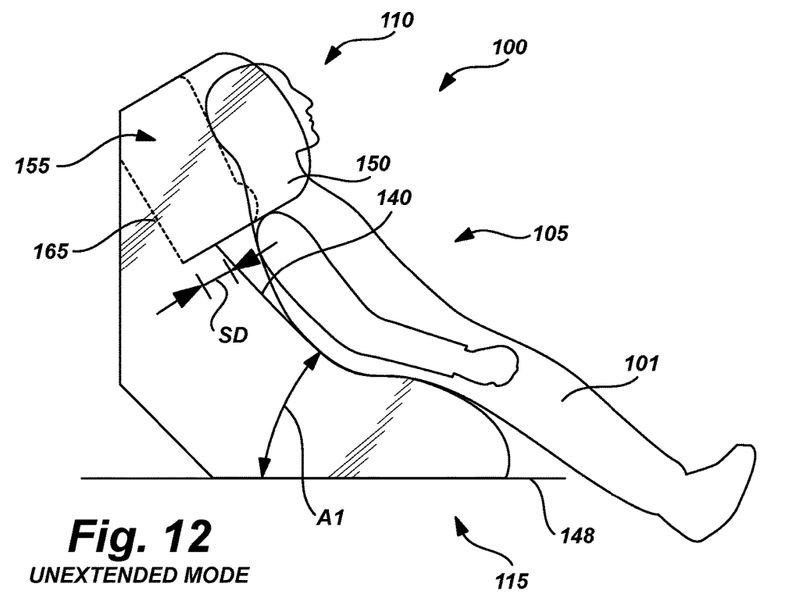
FIG. 12 is a side view of an exemplary embodiment of the present invention.

Body assembly 115 may include shaped surfaces to facilitate the comfort of a user supported on body assembly 115 such as, for example, a curved portion 135 and an angled surface 140. Curved portion 135 may include a convex curvature that may curve outward for comfortably supporting a user's body. Angled surface 140 may be angled relative to a bottom surface 145 of body assembly 115. Bottom surface 145 may be a substantially flat surface that may be supported by a support surface 148 (e.g., a flat support surface) such as a bed, floor, chair, or any other suitable surface (e.g., as illustrated in FIGS. 10-12). Returning to FIGS. 1-7, angled surface 140 may be angled relative to bottom surface 145 at an angle A1. Angle A1 may be any suitable angle for facilitating comfortable support of a user's body for example when the user is resting, sitting, and/or sleeping. Angle A1 may be between about 20 degrees and about 70 degrees, between about 25 degrees and about 65 degrees, between about 30 degrees and about 60 degrees, between about 40 degrees and about 50 degrees, between about 42 degrees and about 48 degrees, between about 44 degrees and about 46 degrees (e.g., about 45 degrees), or any other suitable angle.

Body assembly 115 may be formed from a plurality of members that may be attached together via any suitable technique such as, for example, adhesive, stitching, fabric welding, mechanical fasteners (e.g., screws or bolts), and/or any other suitable type of attachment technique. Portions of body assembly 115 may also be integrally formed together as a single member. For example, body assembly 115 may be formed via injection-molding (e.g., any suitable injection-molded material such as memory foam and/or any other suitable material for example as described herein).

Head assembly 110 may be shaped, dimensioned, and/or configured in any suitable shape for comfortably supporting a user's head for example to facilitate rest, comfort, and/or sleep of the user. Head assembly 110 may include a plurality of wing members 150 and a support member 155. Wing members 150 and support member 155 may be formed from a plurality of members that may be attached together via any suitable technique such as, for example, adhesive, stitching, fabric welding, mechanical fasteners (e.g., screws or bolts), and/or any other suitable type of attachment technique. Wing members 150 and support member 155 may also be integrally formed together as a single member. Wing members 150 may include a curved surface 152 that may be a convex surface. Head assembly 110 may be formed via injection-molding (e.g., any suitable injection-molded material such as memory foam and/or any other suitable material for example as described herein).

Wing members 150 may be shaped, dimensioned, and/or configured in any suitable shape for comfortably supporting a user's head for example to facilitate rest, comfort, and/or sleep of the user. For example, wing members 150 may be formed with a depth D2, a width W2, and a height H2. Depth D2 may be any suitable dimension for comfortably supporting a user's head such as, for example, between about 4 inches and about 10 inches, between about 6 inches and about 9 inches, or between about 8 inches and about 9 inches. Width W2 may be any suitable dimension for comfortably supporting a user's head such as, for example, between about 2 inches and about 10 inches, between about 3 inches and about 8 inches, or between about 4 inches and about 7 inches. Height H2 may be any suitable dimension for comfortably supporting a user's head such as, for example, between about 4 inches and about 10 inches, between about 6 inches and about 9 inches, or between about 7 inches and about 9 inches (e.g., about 8 inches).

Support member 155 may be shaped, dimensioned, and/or configured in any suitable shape for comfortably supporting a user's head for example to facilitate rest, comfort, and/or sleep of the user. For example, support member 155 may be formed with a depth D3, a width W3, and a height H3. Depth D3 may be any suitable dimension for comfortably supporting a user's head such as, for example, between about 2 inches and about 10 inches, between about 3 inches and about 8 inches, or between about 4 inches and about 7 inches. Width W3 may be any suitable dimension for comfortably supporting a user's head such as, for example, between about 2 inches and about 10 inches, between about 3 inches and about 8 inches, or between about 5 inches and about 7 inches. Height H3 may be any suitable dimension for comfortably supporting a user's head such as, for example, between about 4 inches and about 10 inches, between about 6 inches and about 9 inches, or between about 7 inches and about 9 inches (e.g., about 8 inches).

Wing members 150 and support member 155 may provide for a user's head to remain relatively stationary (e.g., substantially stationary) when the user is supported by apparatus 105. For example, wing members 150 and support member 155 may form a recess 160 (e.g., a receptacle) for receiving a head of a user being supported by apparatus 105.

Wing members 150 and support member 155 may be separate members attached by any suitable attachment technique for example as described herein or may be integral portions of a single member. For example, wing members 150 and support member 155 may be one or more members configured to form recess 160. Based on the user's head being received in recess 160, the user's head may not slide off from or out of head assembly 110 for example when the user may be sleeping. The user's head may thereby remain relatively stationary based on support of the user's head in recess 160 for example when the user is supported by apparatus 105 while resting or sleeping. Apparatus 105 may thereby operate to maintain a user's head stationary in a desirable (e.g., and comfortable) position for treating sleeping disorders and/or maintaining a beneficial position for rest and/or sleep.

Head assembly 110 may be attached to body assembly 115 at an attachment portion 165. Head assembly 110 may be attached to body assembly 115 at attachment portion 165 via any suitable technique such as, for example, adhesive, stitching, fabric welding, mechanical fasteners (e.g., screws or bolts), and/or any other suitable type of attachment technique. For example, a rear portion of wing members 150 and/or support member 155 may be attached to body assembly 115 at attachment portion 165. Apparatus 105 may have any suitable overall height H for comfortably supporting a user's body for example to facilitate rest, comfort, and/or sleep of the user. Overall height H may be, for example, between about 12 inches and about 30 inches, between about 15 inches and about 25 inches, or between about 18 inches and about 22 inches.

A slit 170 may be formed between head assembly 110 and body assembly 115. Head assembly 110 and body assembly 115 may not be attached at slit 170. Head assembly 110 may abut against and be supported by body assembly 115 at slit 170 for example as illustrated in FIG. 2A). For example as illustrated in FIG. 2A, a bottom portion 110a of head assembly 110 (e.g., of wing members 150 and/or support member 155) may selectively abut against and be supported by a support portion 115a of body assembly 115 (e.g., supported in bearing). Slit 170 may extend across some of a width or a substantially entire width of apparatus 105 between head assembly 110 and body assembly 115 (e.g., across some or all of widths W1, W2, and W3). In at least some exemplary embodiments, slit 170 may extend across a substantially entire width of apparatus 105 between head assembly 110 and body assembly 115 (e.g., across all of widths W1, W2, and W3). Slit 170 may have any suitable slit depth SD to provide for the exemplary disclosed operation for example as described herein. Slit depth SD may be between about 0.5 inches and about 4 inches, between about 1 inch and about 3 inches, between about 1 inch and about 2 inches, or any other suitable slit depth. In at least some exemplary embodiments, slit depth SD may be about 1.5 inches.

Figure 8:
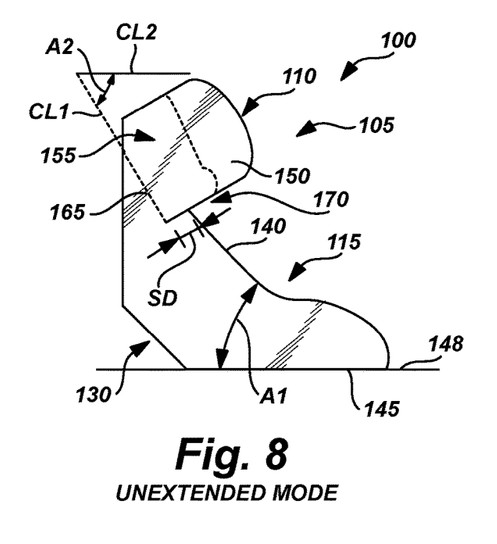
FIG. 8 is a side view of an exemplary embodiment of the present invention.
Figure 9:
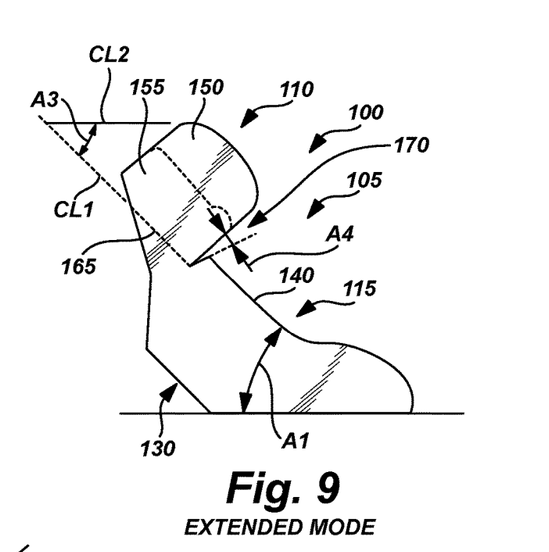
FIG. 9 is a side view of an exemplary embodiment of the present invention.
Figure 9A:
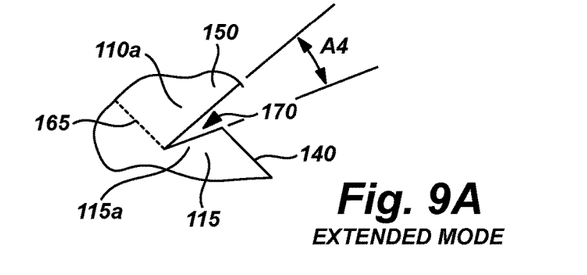
FIG. 9A is a detailed, side view of an exemplary embodiment of the present invention.

Head assembly 110 may be selectively moved relative to body assembly 115 between an unextended mode for example as illustrated in FIGS. 2A and 8 and an extended mode for example as illustrated in FIGS. 9 and 9A. When apparatus 105 is not subjected to a force such as force from a user, head assembly 110 may be disposed in the unextended mode for example as illustrated in FIGS. 2A and 8 (e.g., a rest mode or an "at rest" mode).

Figure 2:
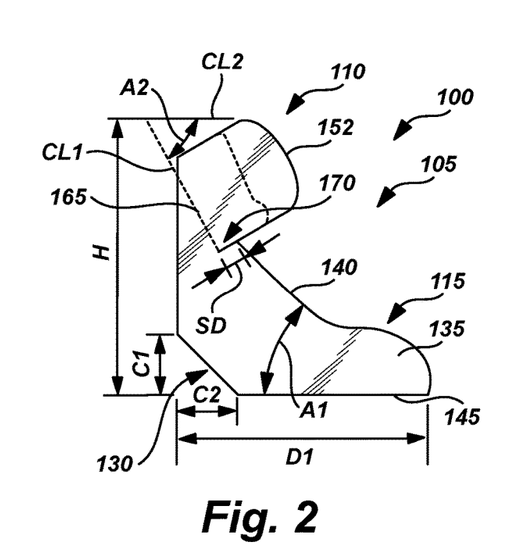
FIG. 2 is a side view of an exemplary embodiment of the present invention.
Figure 2A:
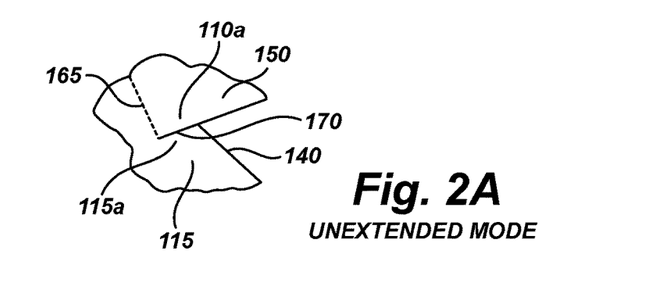
FIG. 2A is a detailed, side view of an exemplary embodiment of the present invention.
Figure 3:
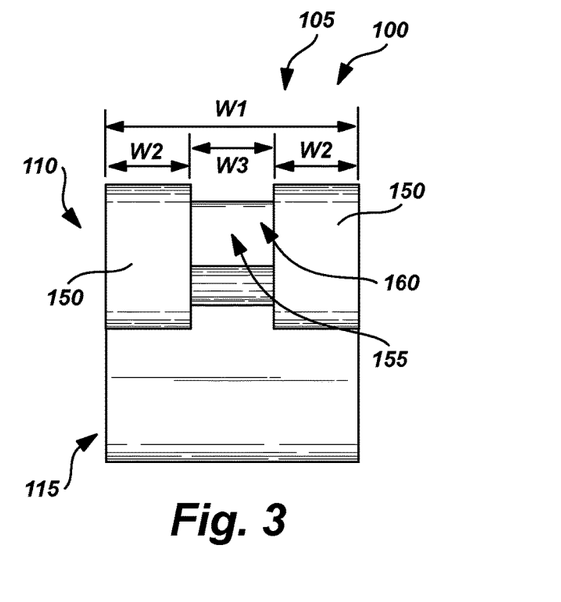
FIG. 3 is a front view of an exemplary embodiment of the present invention.
Figure 4:
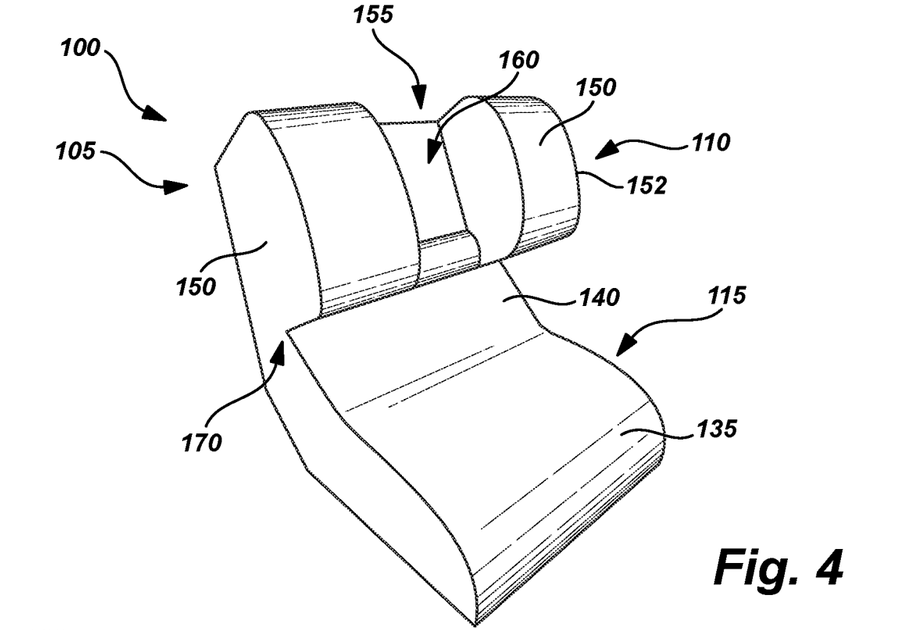
FIG. 4 is a perspective view of an exemplary embodiment of the present invention.
Figure 5:
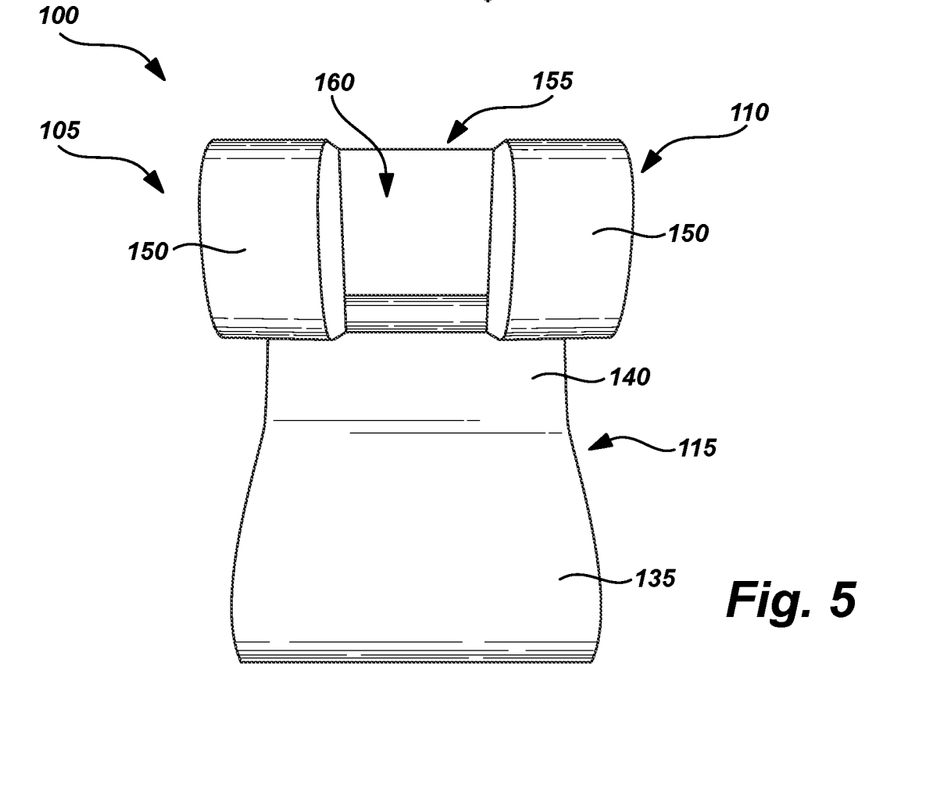
FIG. 5 is a front view of an exemplary embodiment of the present invention.
Figure 6:
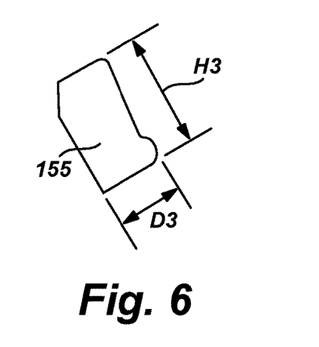
FIG. 6 is a side view of an exemplary embodiment of the present invention.
Figure 7:
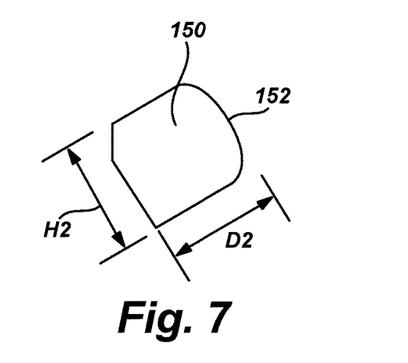
FIG. 7 is a side view of an exemplary embodiment of the present invention.

When head assembly 110 is in the unextended mode for example as illustrated in FIGS. 2 and 8, head assembly 110 may be disposed at a head assembly angle A2. Head assembly angle A2 may be measured between an attachment centerline CL1 of attachment portion 165 and a horizontal topline CL2 of apparatus 105. Attachment centerline CL1 may be a centerline of attachment portion 165 attaching head assembly 110 and body assembly 115 (e.g., a line or plane at which a rear of wing members 150 and support member 155 may contact and be attached to body assembly 115). Horizontal topline CL2 may be a horizontal line disposed at a top of apparatus 105 and may be parallel to bottom surface 145 and/or support surface 148.

Head assembly angle A2 may be any suitable angle for supporting a user's head for example to facilitate rest, comfort, and/or sleep of the user. For example, head assembly angle A2 may be between about 55 degrees and about 85 degrees (e.g., or 90 degrees), between about 60 degrees and about 75 degrees, between about 60 degrees and about 70 degrees, between about 64 degrees and about 68 degrees (e.g., about 66 degrees), or any other suitable angle. In at least some exemplary embodiments, head assembly angle A2 may provide for a Fowler position (e.g., High Fowler position). For example, angle A1 and head assembly angle A2 may provide for a user to sit up using apparatus 105. In at least some exemplary embodiments, angle A1 and head assembly angle A2 may provide for suitable chest expansion and breathing by facilitating oxygenation of a user supported by apparatus 105, thereby providing a suitable user position to address (e.g., treat) respiratory distress syndrome.

When head assembly 110 is in the extended mode for example as illustrated in FIGS. 9 and 9A, head assembly 110 may be disposed at an extended head assembly angle A3 and slit 170 may be opened at a slit opening angle A4. For example, slit 170 may be selectively closed (e.g., in a closed position) as illustrated in FIG. 2A and selectively opened (e.g., in an open position) as illustrated in FIG. 9A. When head assembly 110 is moved relative to body assembly 115 from the unextended mode illustrated in FIGS. 2A and 8 to the extended mode illustrated in FIGS. 9 and 9A, head assembly 110 may remain attached to body assembly 115 via attachment portion 165, with attachment portion 165 deflecting based on a force (e.g., force from a user) causing the movement from the unextended mode to the extended mode. As illustrated in FIGS. 8 and 9, attachment portion 165 and attachment centerline CL1 may deflect and/or rotate based on head assembly 110 moving (e.g., deflecting and/or rotating) from the unextended mode illustrated in FIG. 8 to the extended mode illustrated in FIG. 9. In doing so, an angle between attachment centerline CL1 and horizontal topline CL2 may change from head assembly angle A2 to extended head assembly angle A3. Extended head assembly angle A3 may be less than the exemplary disclosed angles above of head assembly angle A2 by between about 5 degrees and about 25 degrees, between about 10 degrees and about 20 degrees, between about 12 degrees and about 18 degrees, or between about 14 degrees and about 16 degrees (e.g., about 15 degrees). For example, head assembly angle A3 may be between about 40 degrees and about 70 degrees, between about 45 degrees and about 60 degrees, between about 45 degrees and about 55 degrees, between about 49 degrees and about 53 degrees (e.g., about 51 degrees), or any other suitable angle. Force may be applied for example by a user to move head assembly 110 from head assembly angle A2 to extended head assembly angle A3 when a user becomes positioned in apparatus 105 for example as described further below.

When head assembly 110 is moved relative to body assembly 115 from the unextended mode illustrated in FIGS. 2A and 8 to the extended mode illustrated in FIGS. 9 and 9A, slit opening angle A4 may be formed between bottom portion 110a of head assembly 110 and support portion 115a of body assembly 115. Slit opening angle A4 may be any suitable angle for facilitating movement of head assembly 110 from the unextended mode to the extended mode such as, for example, between about 5 degrees and about 25 degrees, between about 10 degrees and about 20 degrees, between about 12 degrees and about 18 degrees, or between about 14 degrees and about 16 degrees (e.g., about 15 degrees).

In at least some exemplary embodiments, a surface of support member 155 configured to support a head of a user may be angled relative to angled surface 140 when slit 170 is in the closed position. For example, the surface of support member 155 configured to support the head of the user may be angled relative to angled surface 140 when slit 170 is in the closed position at an angle of between about 4 degrees and about 24 degrees, between about 10 degrees and about 20 degrees, between about 12 degrees and about 18 degrees, or between about 14 degrees and about 16 degrees.

The exemplary disclosed system, apparatus, and method may be used in any suitable application for supporting a user's body. For example, the exemplary disclosed system, apparatus, and method may be used in any suitable application for supporting a user's body during sleep. The exemplary disclosed system, apparatus, and method may be used in any suitable application for supporting an upper body of a human. The exemplary disclosed system, apparatus, and method may be used in any suitable application for treating and substantially preventing sleeping conditions and disorders such as snoring and sleep apnea.

Figure 16:
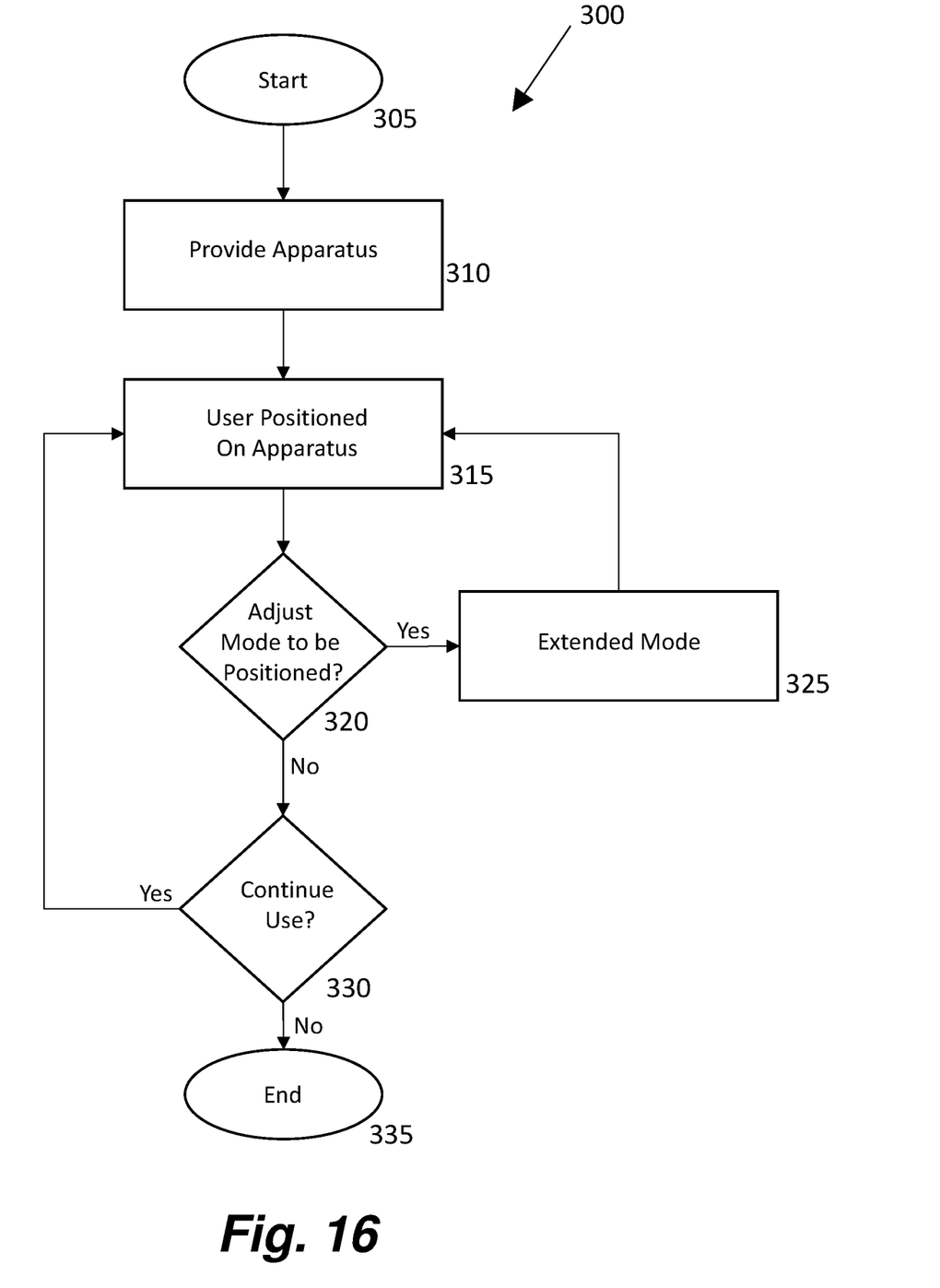
FIG. 16 illustrates an exemplary process of at least some exemplary embodiments of the present disclosure.

FIG. 16 illustrates an exemplary operation of the exemplary disclosed system 100. Process 300 begins at step 305. At step 310, a user 101 (e.g., a human body for example as illustrated in FIGS. 11 and 12) may be provided with apparatus 105. At step 315, user 101 may utilize apparatus 105 for example by sitting, resting, laying, and/or sleeping on apparatus 105. For example at step 315, user 101 may be positioned on apparatus 105. Apparatus 105 may be in the unextended mode illustrated for example in FIG. 10 when user 101 is provided with and initially utilizes apparatus 105. User 101 may be any suitable user of apparatus 105 such as, for example, an adult, a child, a young adult, a baby, an elderly person, or any other suitable user.

Returning to FIG. 16, at step 320, user 101 may determine whether or not a mode of apparatus 105 is to be changed or adjusted as user 101 is positioned on apparatus 105. If the mode is to be adjusted, process 300 may proceed to step 325.

At step 325 and for example as illustrated in FIG. 11, user 101 may apply a force to head assembly 110 to move head assembly 110 from the exemplary disclosed unextended mode to the exemplary disclosed extended mode. For example, user 101 may sit or lean against apparatus 105 and may push up a lower portion of head assembly 110 for example using the user's shoulder. Slit 170 may operate (e.g., open, for example as described herein) to provide a desired amount of rotation of head assembly 110 relative to body assembly 115 (e.g., between head assembly 110 and body assembly 115). Based on an operation of slit 170 (e.g., slit 170 opening to slit opening angle A4), user 101 may move head assembly 110 from the unextended mode for example as illustrated in FIG. 10 to the extended mode for example as illustrated in FIG. 11 without strain or discomfort (e.g., user 101 may move head assembly 110 using a comfortable exertion of force based on a presence and an opening operation of slit 170). Also for example, another user and/or any suitable mechanical device such as a mechanical actuator (e.g., piston) may move head assembly 110 or assist with a movement of head assembly 110 (e.g., based on slit 170 opening to slit opening angle A4). As head assembly 110 is maintained (e.g., comfortably maintained) in the extended mode for example as illustrated in FIGS. 9, 9A, and 11, user 101 may position the user's body in a comfortable position. When user 101 is finished positioning the user's body comfortably, user 101 may cease or stop exerting the force against head assembly 110. Head assembly 110 may flexibly or elastically return to the unextended mode for example as illustrated in FIGS. 2, 2A, and 12. For example, elastic (e.g., flexible) properties of the exemplary disclosed materials and the exemplary disclosed configuration provided by attachment portion 165 may return head assembly 110 from the exemplary disclosed extended mode to the exemplary disclosed unextended mode. For example, apparatus 105 may store potential energy when user 101 applies force to move head assembly 110 from the unextended mode to the extended mode, and then the potential energy may be released when the user's force or resistance is removed to return head assembly 110 from the extended mode to the unextended mode. Process 300 may then return to step 315 and user 101 may remain positioned on and supported by apparatus 105 to facilitate sitting, resting, laying, and/or sleeping by user 101.

Returning to FIG. 16, if the mode is not to be adjusted by user 101 (e.g., and/or another user or device) at step 320, process 300 may proceed to step 330. User 101 may determine whether or not to continue use of apparatus 105. If user 101 decides to continue use of apparatus 105, process 300 may return to step 315. If user 101 decides not to continue use of apparatus 105, process 300 ends at step 335.

Figure 13:
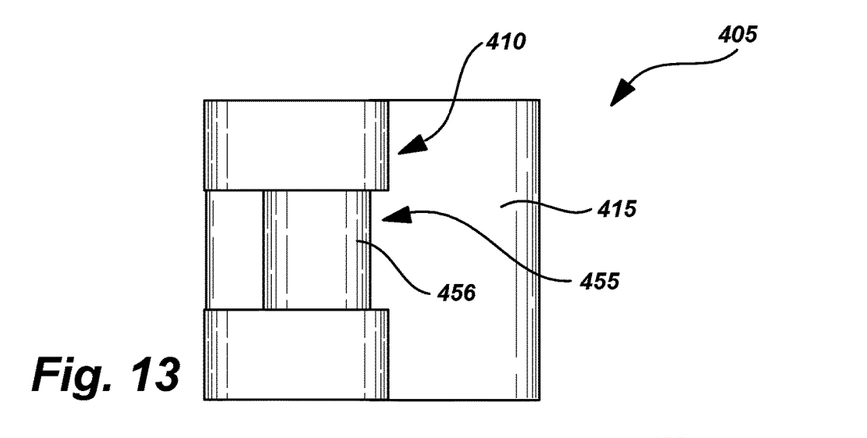
FIG. 13 is a top view of an exemplary embodiment of the present invention.
Figure 14:
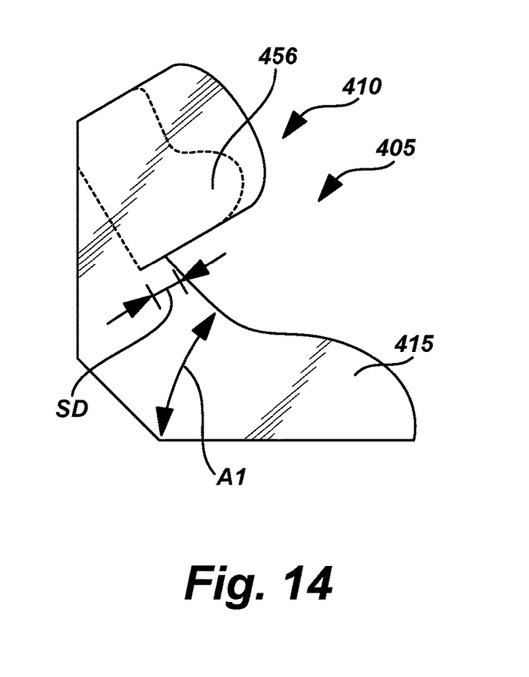
FIG. 14 is a side view of an exemplary embodiment of the present invention.
Figure 15:
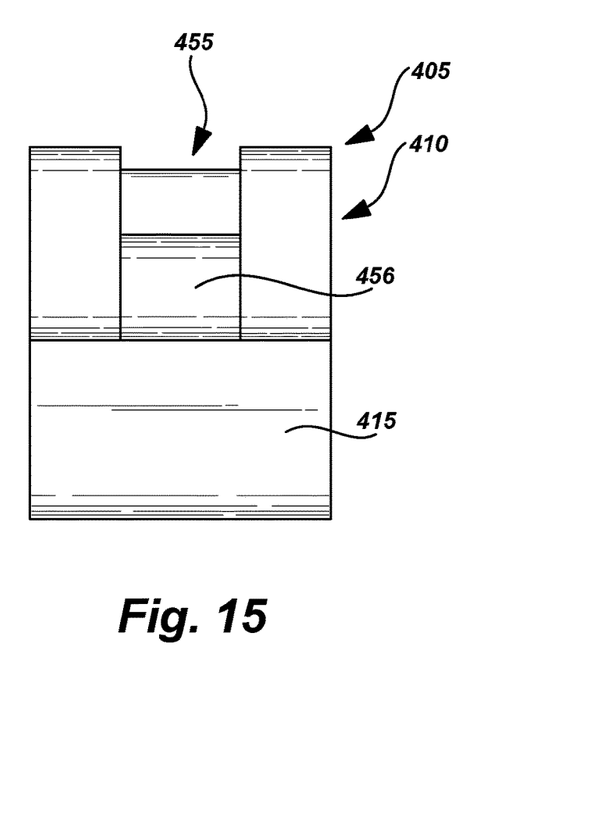
FIG. 15 is a front view of an exemplary embodiment of the present invention.

FIGS. 13-15 illustrate another exemplary embodiment of the exemplary disclosed system, apparatus, and method. Apparatus 405 may be generally similar to apparatus 105, and may include a head assembly 410 that may be generally similar to head assembly 110 and a body assembly 415 that may be generally similar to body assembly 115. Head assembly 410 may include a support member 455 that may have a bottom protruding portion 456 that may extend out to provide comfort to a back of a head and/or neck of user 101. Apparatus 405 may be used similarly to as described above regarding process 300.

In at least some exemplary embodiments, the exemplary disclosed apparatus may be angled at multiple angles or inclinations (e.g., angle A1 and head assembly angle A2), which may provide additional comfort to a user (e.g., as compared to a single angle in at least some exemplary embodiments). For example, a user's back may be supported at angle A1 and a user's head may be supported at head assembly angle A2.

In at least some exemplary embodiments, the exemplary disclosed apparatus may be an apparatus for supporting a human body. The apparatus may include a body assembly (e.g., body assembly 115 or body assembly 415) configured to support a back of the human body, a head assembly (e.g., head assembly 110 or head assembly 410) attached to the body assembly via an attachment portion, the head assembly including one or more members forming a recess configured to receive a head of the human body, and a slit disposed between the body assembly and the head assembly, the slit configured to open from a closed position to an open position to provide rotation of the head assembly relative to the body assembly. The slit may extend across a width of the body assembly and the head assembly. The slit may be disposed adjacent to the attachment portion and may extend along a length of the attachment portion. The slit may be formed between a bottom portion of the head assembly and a support portion of the body assembly that supports the bottom portion of the head assembly when the slit is in the closed position. The one or more members may include a plurality of wing members forming walls of the recess and a support member disposed between the wing members and configured to support the head. A surface of the support member supporting the head may be angled at the High Fowler position relative to a bottom surface of the apparatus. A centerline of the attachment portion may be angled at between 60 and 70 degrees from a horizontal topline disposed at a top of the apparatus when the slit is in the closed position, the horizontal topline being parallel to a bottom surface of the apparatus. A surface of the body assembly configured to support the back may be angled at between 42 degrees and 48 degrees from the bottom surface. A slit opening angle of the slit when the slit is in the open position may be between 12 degrees and 18 degrees. The body assembly and the head assembly may be formed from viscoelastic memory foam.

In at least some exemplary embodiments, the exemplary disclosed method may be a method for supporting a human body. The method may include providing an apparatus including a body assembly (e.g., body assembly 115 or body assembly 415) and a head assembly (e.g., head assembly 110 or head assembly 410) attached to the body assembly via an attachment portion, the apparatus including a slit disposed between the body assembly and the head assembly, supporting a back of the human body with the body assembly, supporting a head of the human body with the head assembly, rotating the head assembly relative to the body assembly based on opening and closing the slit between a closed position and an open position, and maintaining the head in the head assembly based on receiving the head in a recess formed in the head assembly. Receiving the head in the recess may include maintaining the head in the recess between two wing members that form side walls of the recess. Receiving the head in the recess may include maintaining the head in the recess during a sleep state of the human body. Supporting the back of the human body with the body assembly may include supporting the back on a surface of the body assembly that is angled at between 44 degrees and 46 degrees from a bottom surface of the apparatus. Supporting the head of the human body with the head assembly may include supporting the head on a surface of the head assembly that is angled at between 64 and 68 degrees from a horizontal topline disposed at a top of the apparatus, the horizontal topline being parallel to a bottom surface of the apparatus. The open position of the slit may be formed by a slit opening angle of 15 degrees. The exemplary disclosed method may further include rotating the head assembly relative to the body assembly based on opening the slit from the closed position to the open position using shoulders of the human body to urge a bottom portion of the head assembly.

In at least some exemplary embodiments, the exemplary disclosed apparatus may be an apparatus for supporting a human body. The apparatus may include a body assembly (e.g., body assembly 115 or body assembly 415) configured to support a back of the human body, a head assembly (e.g., head assembly 110 or head assembly 410) attached to the body assembly via an attachment portion, the head assembly including one or more members forming a recess configured to receive a head of the human body, and a slit disposed between the body assembly and the head assembly, the slit configured to open from a closed position to an open position to provide rotation of the head assembly relative to the body assembly. A centerline of the attachment portion may be angled at between 64 and 68 degrees from a horizontal topline disposed at a top of the apparatus when the slit is in the closed position, the horizontal topline being parallel to a bottom surface of the apparatus. A surface of the body assembly configured to support the back may be angled at between 42 degrees and 48 degrees from the bottom surface. A slit opening angle of the slit when the slit is in the open position may be between 12 degrees and 18 degrees. A surface of the head assembly configured to support the head may be angled at between 10 and 20 degrees relative to the surface of the body assembly configured to support the back when the slit is in the closed position. The centerline of the attachment portion may be angled at 66 degrees from the horizontal topline. The surface of the body assembly may be angled at 45 degrees from the bottom surface. The slit opening angle may be 15 degrees when the slit is in the open position.

In at least some exemplary embodiments, the exemplary disclosed system, apparatus, and method may provide an efficient and effective system for treating and substantially preventing sleeping conditions and disorders such as snoring and sleep apnea. For example, the exemplary disclosed system, apparatus, and method may maintain a user's head in a stationary position during sleep, which may be beneficial in treating and substantially preventing such conditions. The exemplary disclosed system, apparatus, and method may also allow for a user to adjustably attain a stationary position of the user's head.

It will be apparent to those skilled in the art that various modifications and variations can be made to the exemplary disclosed system, apparatus, and method. Other embodiments will be apparent to those skilled in the art from consideration of the specification and practice of the exemplary disclosed apparatus, system, and method. It is intended that the specification and examples be considered as exemplary, with a true scope being indicated by the following claims.

What is claimed is:

1. An apparatus for supporting a human body, comprising:
   a body assembly configured to support a back of the human body;
   a head assembly attached to the body assembly via an attachment portion, the head assembly including one or more members forming a recess configured to receive a head of the human body; and
   a slit disposed between the body assembly and the head assembly, the slit configured to open from a closed position to an open position to provide rotation of the head assembly relative to the body assembly;
   wherein a slit opening angle of the slit when the slit is in the closed position is 0 degrees.

2. The apparatus of claim 1, wherein the slit extends across a width of the body assembly and the head assembly.

3. The apparatus of claim 1, wherein the slit is disposed adjacent to the attachment portion and extends along a length of the attachment portion.

4. The apparatus of claim 1, wherein the slit is formed between a bottom portion of the head assembly and a support portion of the body assembly that supports the bottom portion of the head assembly when the slit is in the closed position.

5. The apparatus of claim 1, wherein the one or more members include a plurality of wing members forming walls of the recess and a support member disposed between the wing members and configured to support the head.

6. The apparatus of claim 1, wherein a centerline of the attachment portion is angled at between 60 and 70 degrees from a horizontal topline disposed at a top of the apparatus when the slit is in the closed position, the horizontal topline being parallel to a bottom surface of the apparatus.

7. The apparatus of claim 6, wherein a surface of the body assembly configured to support the back is angled at between 42 degrees and 48 degrees from the bottom surface.

8. The apparatus of claim 1, wherein the slit opening angle of the slit when the slit is in the open position is between 12 degrees and 18 degrees.

9. The apparatus of claim 1, wherein the body assembly and the head assembly are formed from viscoelastic memory foam.

10. A method for supporting a human body, comprising:
providing an apparatus including a body assembly and a head assembly attached to the body assembly via an attachment portion, the apparatus including a slit disposed between the body assembly and the head assembly;
supporting a back of the human body with the body assembly;
supporting a head of the human body with the head assembly;
rotating the head assembly relative to the body assembly based on opening and closing the slit between a closed position and an open position;
maintaining the head in the head assembly based on receiving the head in a recess formed in the head assembly; and
abutting the head assembly against the body assembly when the slit is in the closed position.

11. The method of claim 10, wherein receiving the head in the recess includes maintaining the head in the recess between two wing members that form side walls of the recess.

12. The method of claim 10, wherein receiving the head in the recess includes maintaining the head in the recess during a sleep state of the human body.

13. The method of claim 10, wherein supporting the back of the human body with the body assembly includes supporting the back on a surface of the body assembly that is angled at between 44 degrees and 46 degrees from a bottom surface of the apparatus.

14. The method of claim 10, wherein supporting the head of the human body with the head assembly includes supporting the head on a surface of the head assembly that is angled at between 64 and 68 degrees from a horizontal topline disposed at a top of the apparatus, the horizontal topline being parallel to a bottom surface of the apparatus.

15. The method of claim 10, wherein the open position of the slit is formed by a slit opening angle of 15 degrees.

16. The method of claim 10, further comprising rotating the head assembly relative to the body assembly based on opening the slit from the closed position to the open position using shoulders of the human body to urge a bottom portion of the head assembly.

17. The method of claim 10, further comprising:
storing potential energy when the head assembly moves from the closed position to the open position; and
returning the head assembly from the open position to the closed position based on releasing the potential energy.

18. An apparatus for supporting a human body, comprising:
a body assembly configured to support a back of the human body;
a head assembly attached to the body assembly via an attachment portion, the head assembly including one or more members forming a recess configured to receive a head of the human body; and
a slit disposed between the body assembly and the head assembly, the slit configured to open from a closed position to an open position to provide rotation of the head assembly relative to the body assembly;
wherein a centerline of the attachment portion is angled at between 64 and 68 degrees from a horizontal topline disposed at a top of the apparatus when the slit is in the closed position, the horizontal topline being parallel to a bottom surface of the apparatus;
wherein a surface of the body assembly configured to support the back is angled at between 42 degrees and 48 degrees from the bottom surface; and
a slit opening angle of the slit when the slit is in the open position is between 12 degrees and 18 degrees;
wherein when the slit is in the closed position, the slit is completely closed with the head assembly abutting flush against the body assembly.

19. The apparatus of claim 18, wherein a surface of the head assembly configured to support the head is angled at between 10 and 20 degrees relative to the surface of the body assembly configured to support the back when the slit is in the closed position.

20. The apparatus of claim 18, wherein:
the centerline of the attachment portion is angled at 66 degrees from the horizontal topline;
the surface of the body assembly is angled at 45 degrees from the bottom surface; and
the slit opening angle is 15 degrees when the slit is in the open position.

* * * * *